United States Patent
Gieslink et al.

(10) Patent No.: US 9,839,184 B2
(45) Date of Patent: Dec. 12, 2017

(54) FAST GROWING PLANTS OF THE FAMILY VIOLACEAE

(71) Applicant: SYNGENTA PARTICIPATIONS AG, Basel (CH)

(72) Inventors: Robbie Gieslink, Enkhuizen (NL); Nico De Haan, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 58 days.

(21) Appl. No.: 14/381,228

(22) PCT Filed: Feb. 27, 2013

(86) PCT No.: PCT/EP2013/053914
§ 371 (c)(1),
(2) Date: Aug. 27, 2014

(87) PCT Pub. No.: WO2013/127839
PCT Pub. Date: Sep. 6, 2013

(65) Prior Publication Data
US 2015/0113872 A1  Apr. 30, 2015

(30) Foreign Application Priority Data
Feb. 28, 2012  (EP) .................... 12157347

(51) Int. Cl.
*A01H 5/02* (2006.01)
(52) U.S. Cl.
CPC ..................... *A01H 5/02* (2013.01)
(58) Field of Classification Search
CPC ............. A01H 5/02; A01H 5/10; A01G 1/001
USPC ..................................... 47/58.1 R
See application file for complete search history.

(56) References Cited

PUBLICATIONS

Merritt et al 1995, Scientia Horticulturae 60: 313-324.*
American Takii Pansy F1 Nature Rose Picotee Sales Flyer dated Dec. 2010 for 2011-2012.*
International Search Report for International Application No. PCT/EP2013/053914, dated Jun. 24, 2013.
Adams et al., "The effects of temperature, photoperiod and light integral on the time to flowering of pansy cv. Universal Violet (Viola X wittrockiana Gams.)", Annals of Botany (London), vol. 80, No. 1, 1997, pp. 107-112, XP002678710.
Johnny's Selected Seeds: "Majestic Giants II Formula Mix F1", Flower Seeds: Viola (Pansy), 2011, XP00267811, Retrieved from the Internet: URL:johnnyseeds.com/p-5551-majestic-giants-ii-formula-mix-fl-aspx [retrieved on Jun. 27, 2012].
Erik Runkle & Royal Heins, Photocontrol of Flowering and Extension Growth in Long-day Plant Pansy, 7 pages, 2003, American Society for Horticultural Science, US.†
S.R. Adams et al., The Effects of Temperature, Photoperiod and Light Integral on the Time to Flowering of Pansy cv. Universal Violet (Viola x wittrockiana Gams.), 6 pages, 1997, Oxford University Press, GB.†
T. Howe & W.E. Waters, Pansy Cultivar Evaluation in the Landscape, 5 pages, 1989, Florida State Horticultural Society, US.†
Jim Nau, Ball Culture Guide: The Encyclopedia of Seed Germination, 3 pages, 1993, Ball Publishing, US.†
Neil Mattson & J. Erwin, Temperature Affects Flower Initiation and Development Rate of Impatiens, Petunia, and Viola, 7 pages, 2003, International Society for Horticultural Science, BE.†

* cited by examiner
† cited by third party

*Primary Examiner* — David H Kruse
(74) *Attorney, Agent, or Firm* — Dale Skalla

(57) ABSTRACT

The present invention relates to a plant of the family Violaceae, in particular to a pansy plant having shortened growing time. In particular, a plant of the invention grows significantly faster than a control plant when grown at the same time and under the same conditions. Methods of growing a pansy plant of the invention and uses thereof are also provided.

5 Claims, No Drawings

FAST GROWING PLANTS OF THE FAMILY VIOLACEAE

FIELD OF THE INVENTION

The present invention relates to plants belonging to the family Violaceae, in particular to pansy plants which require a shorter time in which to reach maturity during spring season.

BACKGROUND

The pansy is a large group of hybrid plants cultivated as garden flowers. Pansies are derived from *Viola* species: *Viola tricolor* hybridized with other viola species, these hybrids are referred to as *Viola×wittrockiana* or less commonly *Viola tricolor hortensis*. The name "pansy" also appears as part of the common name for other *Viola* species that are wildflowers in Europe.

Modern horticulturists have developed a wide range of Pansy flower colors and bicolors including yellow, gold, orange, purple, violet, red, white, and even black (very dark purple), as well as variable colored varieties. Pansies typically display large showy face markings.

Pansies are generally hardy plants and will survive freezing temperatures even during their blooming season. Plants grow well in sunny or partially sunny positions in well-draining soils. Pansies are normally biennials. The first year plant produces greenery, and bears flowers and seeds in its second year of growth. Afterwards, the plant dies like an annual.

Pansies can survive light freezes and short periods of snow cover, but, in areas with prolonged snow cover, a covering of dry winter mulch is recommended. Pansies perform best in zones with moderate temperatures, and equal amounts of mild rainfall and sunshine.

Pansies usually are sold to the end consumer as flowering plants. Regular (biannual) pansies grown into spring respond strongly to daylength and temperature when it comes to flowering timing. Differences in flowering response occur from season to season and variety to variety. This makes it difficult to predict when the pansies will be ready to be sold. It very often happens that the pansies flower either too late or too early. In many cases growers need to take corrective actions like spraying with plant growth regulators, heating or cooling the crop, picking early flowers. Every correction made is costing labour and inputs and an opportunity for failure. In the Netherlands for example, many retail companies have started to sell pansies in spring in specific weeks, and so the need for predictable growing varieties has increased even more.

Therefore a need exists for a pansy plant which grows more uniform and more predictably and requires less input in terms of labor costs and resources.

SUMMARY OF THE INVENTION

The present invention provides a solution to this problem because the pansies described herein display a uniformity within and between varieties. They are also daylength neutral and the spring production cycle is shortened by about 60 days.

The customer is therefore provided with the benefits of having a shorter production cycle, more flexibility in planning, lower risk of mistakes, absolute programmability and no risk of earlier flowering. Significantly less electricity is used for lighting and heating glasshouses. For the consumer, the benefit is clearly the provision of a fresh bedding plant that continues to grow and flower with strong blooms.

The present invention is therefore a unique plant which meets an unmet need amongst pansy growers and end consumers.

The inventors of the present application have surprisingly developed fast growing pansies (*Viola×wittrockiana*) that will flower under low light conditions. When growing these pansies for example at 11° C. day and night, it is possible to grow them for spring season in north western Europe very predictably and up to 30% faster than regular (biennual) pansies.

The present invention therefore provides a pansy plant belonging to the species *Viola×wittrockiana*, characterized in that said plant is capable of reaching maturity within 121 days after sowing (in other words, in 121 days or less). In one embodiment, the present invention provides a plant belonging to the family Violaceae, characterized in that said plant is capable of reaching maturity in less than about 119 days after sowing. In one embodiment, said plant belongs to the genus *Viola*. In another embodiment, said plant is a hybrid pansy. In another embodiment, said plant belongs to the species *Viola×wittrockiana*.

There is also provided a plant according to the invention, wherein said plant is capable of reaching maturity in less than about 113 days after sowing. In one embodiment, said plant is capable of reaching maturity when grown at an average temperature of less than 16° C. In another embodiment, said plant is capable of reaching maturity when grown at an average temperature of less than 14° C. In another embodiment, said plant is capable of reaching maturity when grown at an average temperature of less than 13° C. In another embodiment, said plant is capable of reaching maturity when grown at an average temperature of less than 11° C. In another embodiment, said plant is capable of reaching maturity when grown at an average temperature of less than 8° C.

There is also provided a plant according to the invention, wherein said plant is capable of reaching maturity when grown under conditions of constant light intensity. In one embodiment, said plant is capable of reaching maturity when grown under a constant light intensity of defined PAR.

There is also provided a plant according to the invention, wherein said plant is capable of reaching maturity when grown under conditions of constant air humidity.

There is also provided a plant according to the invention, wherein said plant has at least one open flower at maturity. In one embodiment, at least about 50% of a population of said plant have on average at least one open flower at maturity. In another embodiment, at least about 70% of a population of said plant have on average at least one open flower at maturity.

In one embodiment, said plant reaches maturity at about 121 days or less after sowing. In one embodiment, said plant reaches maturity at about 119 days or less after sowing. In another embodiment, said plant reaches maturity between 89 to 121 days after sowing. In another embodiment, said plant reaches maturity between 89 to 119 days after sowing.

There is provided a plant according to the invention, obtainable by crossing with Speedy Rose Medley, representative seed of which has been deposited at NCIMB under deposit number NCIMB 41931.

There is also provided a plant according to the invention, obtainable by crossing with Speedy True Blue, representative seed of which has been deposited at NCIMB under deposit number NCIMB 41932.

There is also provided a plant according to the invention, wherein said plant is daylength neutral.

There is also provided a plant according to the invention, wherein the lifespan of the plant is annual.

In one embodiment, a plant according to the invention is a hybrid. In one embodiment, said plant is tetraploid. In one embodiment, said plant is an inbred line.

The present invention also provides a plant, wherein said plant is Speedy Rose Medley, representative seed of which has been deposited at NCIMB under deposit number NCIMB 41931.

The present invention also provides a plant, wherein said plant is Speedy True Blue, representative seed of which has been deposited at NCIMB under deposit number NCIMB 41932.

The present invention also provides a plant part of a pansy plant according to the invention.

In one embodiment, said plant part is selected from the group consisting of propagated cuttings, seed and pollen.

There is also provided seed of a pansy plant, wherein said seed when grown into a plant exhibits the distinguishing characteristics of a plant according to the invention.

There is also provided a method of growing a population of hybrid pansy plants belonging to the species *Viola wittrockiana* comprising sowing seed and allowing said population of plants to grow and wherein the time interval between sowing seed and maturity is between 89 and 121 days.

There is also provided a method of growing a population of hybrid pansy plants belonging to the species *Viola wittrockiana* comprising sowing seed and allowing said population of plants to grow and wherein the time interval between sowing seed and maturity is between 89 and 119 days.

In one embodiment, said method further comprises the steps a) the time interval between sowing seed and maturity is 121 days or less; b) the average temperature at which said population is grown is 16° C. or less during the final 98 days of said time interval; and c) at least 50% of said population have at least one or more open flower at maturity.

In one embodiment, said method further comprises the steps a) the time interval between sowing seed and maturity is 119 days or less; b) the average temperature at which said population is grown is 16° C. or less during the final 98 days of said time interval; and c) at least 50% of said population have at least one or more open flower at maturity.

In one embodiment, said method further comprises the steps a) the time interval between sowing seed and maturity is 113 days or less; b) the average temperature at which said population is grown is 16° C. or less during the final 92 days of said time interval; and c) at least 50% of said population have at least one or more open flower at maturity.

In one embodiment, said method further comprises the steps a) the time interval between sowing seed and maturity is 107 days or less; b) the average temperature at which said population is grown is 16° C. or less during the final 86 days of said time interval; and c) at least 50% of said population have at least one or more open flower at maturity.

In one embodiment, said method further comprises the steps a) the time interval between sowing seed and maturity is 101 days or less; b) the average temperature at which said population is grown is 16° C. or less during the final 80 days of said time interval; and c) at least 50% of said population have at least one or more open flower at maturity.

In one embodiment at least 70% of said population have at least one or more open flower at maturity in step c).

In one embodiment the average temperature is 14° C. or less during said time interval in step b).

In one embodiment the average temperature is 13° C. or less during said time interval in step b).

In one embodiment the average temperature is 11° C. or less during said time interval in step b).

In one embodiment the average temperature is 8° C. or less during said time interval in step b).

There is also provided a method according to the invention for growing a plant as described above.

There is also provided the use of a pansy plant or part thereof according to the invention. In one embodiment, said use is as a bedding plant. In another embodiment, said use is as a pot plant.

Definitions

The technical terms and expressions used within the scope of this application are generally to be given the meaning commonly applied to them in the pertinent art of plant breeding and cultivation if not otherwise indicated herein below.

PAR (Photosynthetically active radiation) designates the spectral range (wave band) of solar radiation from 400 to 700 nanometers that photosynthetic organisms are able to use in the process of photosynthesis The maturity of a population of plants according to the invention is taken to mean the growth stage at which at least 50% of said population have at least one open flower.

As used in this specification and the appended claims, the singular forms "a", "an", and "the" include plural referents unless the context clearly dictates otherwise. Thus, for example, reference to "a plant" includes one or more plants.

As used herein, the term "about" when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

A "cultivated pansy plant" is understood within the scope of the invention to refer to a plant that is no longer in the natural state but has been developed by human care and for human use and/or consumption. "Cultivated plants" are further understood to exclude those wild-type species which comprise the trait being subject of this invention as a natural trait and/or part of their natural genetics.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "linkage", and grammatical variants thereof, refers to the tendency of alleles at different loci on the same chromosome to segregate together more often than would be expected by chance if their transmission were independent, in some embodiments as a consequence of their physical proximity. Linkage is measured by percent recombination between loci (centimorgan, cM).

"Locus" is understood within the scope of the invention to refer to a region on a chromosome, which comprises a gene or any other genetic element or factor contributing to a trait.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "population" means a genetically heterogeneous collection of plants sharing a common genetic derivation. A population of plants typically corresponds to 10 or more plants which have more or less the same phenotype at maturity in terms of flower color appearance.

As used herein, the term "progeny" refers to the descendant(s) of a particular cross. Typically, progeny result from breeding of two individuals, although some species (particularly some plants and hermaphroditic animals) can be selfed (i.e. the same plant acts as the donor of both male and female gametes). The descendant(s) can be, for example, of the F1, the F2, or any subsequent generation.

"Trait" is understood within the scope of the invention to refer to a characteristic or phenotype, for example reduced flowering time. A trait may be inherited in a dominant or recessive manner, or may be monogenic or polygenic.

"Dominant" is understood within the scope of the invention to refer to an allele which determines the phenotype when present in the heterozygous or homozygous state.

A "recessive" allele is only displayed when present in the homozygous state.

DETAILED DESCRIPTION OF THE INVENTION

The present application describes a novel pansy plant belonging to the species Viola×wittrockiana. In particular it describes a pansy plant which reaches maturity in a significantly shorter time period than a conventional pansy plant. Due to the shortened growth cycle, a plant of the invention may be called a "speedy" pansy, when compared to a conventional plant.

Typically, the production cycle can be shortened by about 60 days. The benefit to the grower can be seen in terms of uniformity of growth. This means lower risk of mistakes, absolute programmability and no risk of early flowering. For the end consumer, the benefits are that they are provided with a fresh bedding plant that continues to grow and flower with strong blooms.

The present invention thus fulfills an unmet need on the part of pansy growers and of end consumers, particularly those in Northwestern European countries such as the Netherlands and Germany. However, the pansy plants of the present invention can also benefit growers and consumers in other regions of the world.

The present invention provides a plant belonging to the family Violaceae, characterized in that said plant is capable of reaching maturity in less than about 119 days after sowing. In one embodiment, said plant belongs to the genus *Viola*. In one embodiment, said plant is a pansy. In another embodiment, said plant belongs to the species *Viola× wittrockiana*. In another embodiment, said plant belongs to the species *Viola tricolor*. In another embodiment, said plant belongs to the species *Viola lutea*.

The main benefit of the speedy phenotype is the shortened length of time between sowing and maturity at the grower.

Shortened growing time serves to limit the chances of the plant suffering any one of several diseases which are common to pansies. These diseases include stem rot, also known as pansy sickness, caused by a soil-borne fungus. Another disease is leaf spot (*Ramularia deflectens*) which is also a fungal infection. Another disease is mildew caused by stagnant air and can be limited but not necessarily eliminated by spraying (especially leaf undersides). Pansies are also at risk from pests such as slugs and snails which can feed on foliage and from aphids which transmit cucumber mosaic virus leading to stunted growth and yellow veining. Thus in one embodiment, the plant of the invention is at reduced risk of succumbing to any one of the abovementioned diseases or pests.

In terms of morphology, conventional pansies at maturity are up to 10 cm in diameter and have two slightly overlapping upper petals, two side petals, and a single bottom petal with a slight beard emanating from the flower's center. Flowers are produced in a wide range of colors and bicolors. The plant may grow to 20 cm in height, and prefers sun to varying degrees and well-draining soils. Smaller and larger flowering cultivars are available.

The speedy pansy can easily be distinguished from a conventional pansy, for example, by its ability to reach maturity in a significantly shorter time period.

Pansy plants are generally able to be sold by the grower when at least 50% of a population of said plants have at least one open flower, preferably at least 70% of said population.

Thus, there is also provided a plant according to the invention, wherein said plant is capable of reaching maturity in less than about 119 days after sowing, preferably in less than about 113 days after sowing, more preferably in less than about 107 days after sowing, most preferably about 101 days after sowing.

Cultivation of conventional pansies typically involves several stages. These may include plug production using a well-drained, disease-free media. It is recommended at sowing to help maintain humidity around the germinating seed for better germination performance. Germination takes approximately a few days. Light is generally not required for germination. Conventional pansies very often require plant growth regulators (PGRs). The plugs should then be transplanted at the correct time in order to avoid flower bud initiation in the plug stage.

Speedy pansies have the advantage that less plant growth regulators are required than for conventional pansies.

In one embodiment, said plant is capable of reaching maturity when grown under conditions of average temperature. In another embodiment, said plant is capable of reaching maturity when grown at an average temperature of 16° C. or less, more preferably at average 14° C. or less, even more preferably at 13° C. or less, even more preferably at average 11° C. or less, or most preferably at average 8° C. or less. It is known that for conventional pansies, not enough daylight hours leads to unfinished development and the occurrence of small white buds. However, the inventors of the present invention have surprisingly found that speedy pansies are less responsive to shortened daylight hours, and are generally insensitive to low light.

There is also provided a plant according to the invention, wherein said plant is capable of reaching maturity when grown under conditions of constant light intensity. In one embodiment, said plant is capable of reaching maturity when grown under a constant light intensity of defined PAR.

There is also provided a plant according to the invention, wherein said plant is capable of reaching maturity when grown under conditions of average 79% air humidity. In another embodiment said plant is capable of reaching maturity when grown under conditions shown in table 4 and table 5 and weighted average conditions of table 6, or approximating thereto. In one embodiment the growing conditions vary not greater than 10% from those shown in table 4 and table 5 and weighted average conditions of table 6.

There is also provided a plant according to the invention, wherein said plant has at least one open flower at maturity. In one embodiment, at least about 50% of a population of said plant have on average at least one open flower at maturity. In another embodiment, at least about 70% of a population of said plant have on average at least one open flower at maturity.

A typical plant of the invention reaches maturity between 89 days to 121 days after sowing. In another embodiment, said plant reaches maturity between 89 days to 119 days after sowing. In another embodiment, said plant reaches maturity between 89 days to 113 days after sowing. In another embodiment, said plant reaches maturity between 89 days to 107 days after sowing. In another embodiment, said plant reaches maturity between 89 days to 101 days after sowing.

There is also provided a plant according to the invention, obtainable by crossing with Speedy Rose Medley, representative seed of which has been deposited at NCIMB under deposit number NCIMB 41931.

There is also provided a plant according to the invention, obtainable by crossing with Speedy True Blue, representative seed of which has been deposited at NCIMB under deposit number NCIMB 41932.

There is also provided a plant according to the invention, wherein said plant is daylength neutral.

There is also provided a plant according to the invention, wherein the lifespan of the plant is annual.

In one embodiment, a plant according to the invention as described above is a hybrid. In one embodiment, said plant is tetraploid. In one embodiment, said plant is an inbred line. In one embodiment, said plant is vegetatively propagated. In one embodiment, said plant is not a variety.

Results from trials as detailed in the examples show that the Speedy varieties take on average a significantly shorter time to reach maturity compared with conventional pansies. The Speedy varieties which fall within the scope of the invention include Viola×wittrockiana, Blue Bird, Pure white, Pure Yellow, Rose Medley, Light Marina, Light Blue, True Blue, Yellow/Purple, and Rose Medley.

The present invention also provides a plant, wherein said plant is Speedy Rose Medley, representative seed of which has been deposited at NCIMB under deposit number NCIMB 41931. The phenotype of Speedy Rose Medley can be described using the Royal Horticultural Society color scale as follows: 40% 59C (Red-purple group), 30% 71A (Red-purple group), 10% 53A (Red Group), 10% 72B (Red-Purple Group) and 10% N78A (Purple Group)

The present invention also provides a plant, wherein said plant is Speedy True Blue, representative seed of which has been deposited at NCIMB under deposit number NCIMB 41932. The phenotype of Speedy True Blue can be described using the Royal Horticultural Society color scale as follows: 60% 95A (Violet-Blue Group), 30% 93A (Violet-Blue Group), and 10% 95B (Violet-Blue Group).

Speedy Rose Medley, representative seed of which has been deposited at NCIMB under deposit number NCIMB 41931 and Speedy True Blue, representative seed of which has been deposited at NCIMB under deposit number NCIMB 41932 are both identifiable by marker analysis and as such are readily distinguishable from other pansies.

The present invention also provides a plant part of a pansy plant according to the invention.

In one embodiment, said plant part is selected from the group consisting of propagated cuttings, seed and pollen.

There is also provided seed of a pansy plant, wherein said seed when grown into a plant exhibits the distinguishing characteristics of a plant according to the invention.

There is also provided a method of growing a population of hybrid pansy plants belonging to the species Viola wittrockiana according to the invention, comprising sowing seed and allowing said population of plants to grow and wherein the time interval between sowing seed and maturity is between 89 and 121 days.

There is also provided a method of growing a population of hybrid pansy plants belonging to the species Viola wittrockiana according to the invention, comprising sowing seed and allowing said population of plants to grow and wherein the time interval between sowing seed and maturity is between 89 and 119 days.

In one embodiment, said method further comprises the steps a) the time interval between sowing seed and maturity is 121 days or less; b) the average temperature at which said population is grown is 16° C. or less during the final 98 days of said time interval; and c) at least 50% of said population have at least one or more open flower at maturity.

In one embodiment, said method further comprises the steps a) the time interval between sowing seed and maturity is 119 days or less; b) the average temperature at which said population is grown is 16° C. or less during the final 98 days of said time interval; and c) at least 50% of said population have at least one or more open flower at maturity.

In one embodiment, said method further comprises the steps a) the time interval between sowing seed and maturity is 113 days or less; b) the average temperature at which said population is grown is 16° C. or less during the final 92 days of said time interval; and c) at least 50% of said population have at least one or more open flower at maturity.

In one embodiment, said method further comprises the steps a) the time interval between sowing seed and maturity is 107 days or less; b) the average temperature at which said population is grown is 16° C. or less during the final 86 days of said time interval; and c) at least 50% of said population have at least one or more open flower at maturity.

In one embodiment, said method further comprises the steps a) the time interval between sowing seed and maturity is 101 days or less; b) the average temperature at which said population is grown is 16° C. or less during the final 80 days of said time interval; and c) at least 50% of said population have at least one or more open flower at maturity.

In one embodiment at least 70% of said population have at least one or more open flower at maturity in step c).

In one embodiment the average temperature is 14° C. or less during said time interval in step b).

In one embodiment the average temperature is 13° C. or less during said time interval in step b).

In one embodiment the average temperature is 11° C. or less during said time interval in step b).

In one embodiment the average temperature is 8° C. or less during said time interval in step b).

There is also provided a method according to the invention for growing a population of hybrid pansy plants as described above. In one embodiment, the method of the invention is limited to growing a population of plants which are capable of reaching maturity within 121 days, in particular to a population of plants in which at least 50% have at least one open flower within 121 days. In one embodiment, the method of the invention is limited to growing a population of plants which are capable of reaching maturity in less than 119 days, in particular to a population of plants in which at least 50% have at least one open flower in less than 119 days. In one embodiment, the method as described above is used for growing a population of Speedy True Blue, representative seed of which has been deposited at NCIMB under deposit number NCIMB 41932. In one embodiment, the method as described above is used for growing a population of Speedy Rose Medley, representative seed of which has been deposited at NCIMB under deposit number NCIMB 41931. In one embodiment, the population of plants are offered for sale or are sold to the consumer when mature.

In one embodiment, the population of plants is grown in a covered glasshouse. In one embodiment, the sowing date is week 43 to week 45 and the date of maturity is week 9 to week 11 of the following year in North West Europe. Such a population of plants will be ready for the retail market in North West Europe.

There is also provided the use of a glasshouse for growing hybrid pansy plants, wherein a) the time interval between sowing seed and maturity is 121 days or less; b) the average temperature at which said population is grown is 16° C. or less during the final 98 days of said time interval.

There is also provided the use of a glasshouse for growing hybrid pansy plants, wherein a) the time interval between sowing seed and maturity is 119 days or less; b) the average temperature at which said population is grown is 16° C. or less during the final 98 days of said time interval.

In all of the above method embodiments, the method of growing a population of pansy plants specifically excludes the steps of sexually crossing the whole genomes of plants and of subsequently selecting plants.

There is also provided the use of a pansy plant or part thereof according to the invention. In one embodiment, said use is as a bedding plant. In another embodiment, said use is as a pot plant.

Seed Deposit Details

Seed of the variety Speedy True Blue VI171 (a *Viola×wittrockiana* F1 hybrid) has been deposited under the terms of the Budapest Treaty on 1 Feb. 2012 at the NCIMB, Craibstone, Aberdeen, UK under number NCIMB 41932.

Seed of the variety Speedy Rose Medley V1169 (a *Viola×wittrockiana* F1 hybrid) has been deposited under the terms of the Budapest Treaty on 1 Feb. 2012 at the NCIMB, Craibstone, Aberdeen, UK under number NCIMB 41931.

Seed of the variety Speedy Gold with Blotch VL163 (a *Viola×wittrockiana* F1 hybrid) has been deposited under the terms of the Budapest Treaty on 1 Feb. 2012 at the NCIMB, Craibstone, Aberdeen, UK under number NCIMB 41933.

Speedy True Blue represents a sufficient disclosure of a plant of the invention. Speedy Rose Medley represents a sufficient disclosure of a plant of the invention.

EXAMPLE

The following example is presented in order to more fully illustrate some embodiments of the invention. They should in no way be construed, however, as limiting the broad scope of the invention. One skilled in the art can readily devise many variations and modifications of the principles disclosed herein without departing from the scope of the invention.

Example 1

Growth Trials of Speedy Pansies Versus Control Pansies

Seed from speedy pansy and control commercially available pansy varieties was collected from plants in Turkey. Growth trials were initiated at the end of October 2011 in the Netherlands to assess the performance of speedy pansies against control pansies and to quantify grower benefits. Forty thousand plants of each variety were grown. The density was 10 plants per package. The total number of plants used for the trial, including control lines, was five hundred thousand.

The following varieties listed in table 1 below were studied during the grower trial. In the table, the letter "T" signifies a speedy pansy of the invention which has been produced during trial production in Turkey. Varieties denoted as "C" are commercially available. Varieties denoted "6.2" are still experimental and not yet commercially available.

TABLE 1

| T/C | Reference | VARIETY VIOLA WITTROCKIANA | Seeds planted |
|---|---|---|---|
| T | VI163 | EXP. SPEEDY F1 PURE WHITE | 50000 |
| T | VI164 | EXP. SPEEDY F1 YELLOW | 40000 |
| T | VI169 | EXP. SPEEDY F1 ROSE MEDLEY | 40000 |
| T | VI170 | EXP. SPEEDY F1 BLUE | 25000 |
| T | VI171 | EXP. SPEEDY F1 TRUE BLUE | 25000 |
| T | VI183 | EXP. SPEEDY F1 LIGHT MARINA | 25000 |
| C | VL413 | Speedy Blue bird | 25000 |
| T | VL983 | EXP. Speedy Yellow and Purple | 35000 |
| C | VL163 | Delta Gold with Blotch | 40000 |
| C | VM991 | Delta Neon Violet | 25000 |
| C | VK355 | DELTINI(TM) F1 TRUE WHITE | 18000 |
| C | VK570 | DELTINI(TM) F1 BURGUNDY | 32000 |
| C | VK567 | DELTINI(TM) F1 ROSE PINK | 32000 |
| C | VK578 | DELTINI(TM) F1 PURPLE WITH GOLDEN CENTRE | 32000 |
| C | VL452 | DELTINI(TM) F1 BLUE WITH PURPLE WING | 32000 |
| C | VL440 | DELTINI(TM) F1 MICKEY | 32000 |
| 6.2 | VL647 | DELTINI(TM) F1 NEON VIOLET | 32000 |
| 6.2 | VL929 | DELTINI(TM) F1 YELLOW | 18000 |
| 6.2 | VL651 | DELTINI(TM) F1 YELLOW AND PURPLE | 32000 |
| 6.2 | VL927 | EXP. DELTINI(TM) F1 COPPERFIELD | 32000 |
| C | VL436 | EXP. DELTINI F1 VIOLET BLUE | 32000 |

The plants took around 4 weeks in which to appear above the soil line. The plants were transplanted into 8 flats.

During the trials, temperature, humidity and light measurements were taken by watchdogs and recorded on a climate computer. Stationary centres were positioned at ground level. Pictures were taken of all pansies at weekly intervals so that growth could be accurately assessed. Plant growth regulator usage was minimal.

The following climate data were recorded during the growth trial. The $2^{nd}$ column shows the temperature measured in degree Celsius for the date shown in the $1^{st}$ column. The $3^{rd}$ column shows the relative humidity in %.

TABLE 2

| Date | temp Mean | RH Hi |
|---|---|---|
| 1. Nov | 20.2 | 74.7 |
| 2. Nov | 20.3 | 73.2 |
| 3. Nov | 20.2 | 78.9 |
| 4. Nov | 20.3 | 75.5 |
| 5. Nov | 20.2 | 75.3 |
| 6. Nov | 19.9 | 77.3 |
| 7. Nov | 17.9 | 77 |
| 8. Nov | 17.1 | 84.9 |
| 9. Nov | 17.6 | 80.5 |
| 10. Nov | 18.6 | 73 |
| 11. Nov | 17.7 | 72.3 |
| 12. Nov | 17.4 | 72.5 |
| 13. Nov | 17.3 | 73.1 |
| 14. Nov | 17.4 | 73.8 |
| 15. Nov | 16.5 | 68.9 |
| 16. Nov | 16.8 | 66 |
| 17. Nov | 17.1 | 75.7 |
| 18. Nov | 17.8 | 73.3 |
| 19. Nov | 17.6 | 67.3 |
| 20. Nov | 17.4 | 66.7 |
| 21. Nov | 17.4 | 67.9 |
| 22. Nov | 17.9 | 65.9 |
| 23. Nov | 18 | 69.7 |
| 24. Nov | 17.7 | 65.6 |
| 25. Nov | 19.5 | 62.1 |
| 26. Nov | 19.8 | 56.6 |
| 27. Nov | 19.8 | 56.3 |
| 28. Nov | 19.4 | 52.3 |
| 29. Nov | 19.5 | 56.4 |
| 30. Nov | 20.1 | 54.1 |
| 1. Dez | 20.6 | 58.5 |
| 2. Dez | 20.6 | 59 |
| 3. Dez | 20.6 | 57 |
| 4. Dez | 20.9 | 51.1 |
| 5. Dez | 19.9 | 46.5 |
| 6. Dez | 19.8 | 46.8 |
| 7. Dez | 20.6 | 48 |
| 8. Dez | 20 | 74.8 |
| 9. Dez | 13.8 | 65.1 |
| 10. Dez | 12.9 | 69.2 |
| 11. Dez | 13.5 | 70.6 |
| 12. Dez | 14 | 68.4 |
| 13. Dez | 13.5 | 67.1 |
| 14. Dez | 6.5 | 87.6 |
| 15. Dez | 6.7 | 87.9 |
| 16. Dez | 6.4 | 92 |
| 17. Dez | 6.6 | 84.4 |
| 18. Dez | 6.5 | 84.7 |
| 19. Dez | 6.2 | 85.5 |
| 20. Dez | 7.4 | 83.7 |
| 21. Dez | 7.3 | 92.7 |
| 22. Dez | 10 | 90.9 |
| 23. Dez | 9.5 | 90.3 |
| 24. Dez | 7.2 | 86 |
| 25. Dez | 9.7 | 86.3 |
| 26. Dez | 11 | 88.8 |
| 27. Dez | 8.9 | 83.4 |
| 28. Dez | 7.1 | 86.5 |
| 29. Dez | 7.2 | 84.5 |
| 30. Dez | 6.6 | 83.5 |
| 31. Dez | 9.1 | 93.3 |
| 1. Jan | 11.3 | 94.8 |
| 2. Jan | 8.2 | 86.1 |
| 3. Jan | 7.4 | 88.5 |
| 4. Jan | 7.7 | 80.3 |
| 5. Jan | 8.5 | 79.7 |
| 6. Jan | 7.3 | 80.7 |
| 7. Jan | 8.6 | 82 |
| 8. Jan | 8 | 83.8 |
| 9. Jan | 9 | 89.3 |
| 10. Jan | 8.4 | 88.2 |
| 11. Jan | 10 | 90.1 |
| 12. Jan | 10.3 | 85.2 |
| 13. Jan | 10.3 | 78.2 |
| 14. Jan | 10.3 | 78.8 |
| 15. Jan | 10.3 | 82.9 |
| 16. Jan | 10.1 | 87.2 |
| 17. Jan | 10.5 | 77.5 |
| 18. Jan | 10 | 86 |
| 19. Jan | 10.2 | 88.5 |
| 20. Jan | 10.2 | 80.7 |
| 21. Jan | 10.4 | 84.8 |
| 22. Jan | 11 | 86 |
| 23. Jan | 10.6 | 86 |
| 24. Jan | 10.3 | 88 |
| 25. Jan | 10.3 | 86 |
| 26. Jan | 10.3 | 88 |
| 27. Jan | 10.6 | 83 |
| 28. Jan | 10.6 | 88 |
| 29. Jan | 10.6 | 89 |
| 30. Jan | 9.8 | 97 |
| 31. Jan | 10.9 | 94 |
| 1. Feb | 11.4 | 87 |
| 2. Feb | 11.3 | 86 |
| 3. Feb | 10.2 | 96 |
| 4. Feb | 11.7 | 91 |
| 5. Feb | 10.8 | 90 |
| 6. Feb | 12.9 | 95 |
| 7. Feb | 11 | 0 |
| 8. Feb | 10.7 | 94 |
| 9. Feb | 10.6 | 95 |
| 10. Feb | 10.8 | 93 |
| 11. Feb | 11.1 | 92 |
| 12. Feb | 10.7 | 95 |
| 13. Feb | 10.4 | 96 |
| 14. Feb | 10.6 | 92 |
| 15. Feb | 10.7 | 91 |
| 16. Feb | 10.7 | 90 |
| 17. Feb | 10.7 | 98 |
| 18. Feb | 10.6 | 93 |
| 19. Feb | 10.5 | 91 |
| 20. Feb | 11.1 | 94 |
| 21. Feb | 10.8 | 92 |
| 22. Feb | 10.9 | 90 |
| 23. Feb | 11.7 | 97 |
| 24. Feb | 10.6 | 97 |
| 25. Feb | 15.1 | 65.1 |
| 26. Feb | 14.9 | 72.4 |
| 27. Feb | 14.5 | 75.3 |

Speedy True Blue and Speedy Rose Medley were shown to reach maturity (population of plants of each had at least 50% flowering) in less than 119 days when grown under the conditions shown above. Control plants were unable to reach this stage of maturity in the same time frame.

Example 2

Further Growth Trials of Speedy Lines

Plants were sown on Oct. 25, 2012 in Enkhuizen, Netherlands. The following table describes the earliness of the speedy lines versus control lines. Average % of Flowering plants is shown. N=2; 96 plants tested per repetition.

TABLE 3

Sowing date: Oct. 25, 2012

Trial location: Enkhuizen, Netherlands

| Variety name | Variety nr | Feb. 11, 2013 110 | Feb. 13, 2013 112 | Feb. 15, 2013 114 | Feb. 18, 2013 117 | Feb. 20, 2013 119 | Feb. 22, 2013 121 | Remarks |
|---|---|---|---|---|---|---|---|---|
| | | # Days after sow | | | | | | |
| Speedy Pure White | VI163 | 0.0% | 2.1% | 5.7% | 8.3% | 22.9% | 39% | |
| Speedy Yellow | VI164 | 0.0% | 0.0% | 0.0% | 2.1% | 16.7% | 24.5% | |
| Speedy Rose Medley | VI169 | 6.8% | 10.4% | 22.9% | 33.3% | 59.9% | 72.9% | NCIMB deposit nr 41931 |
| Speedy Blue bird | VL413 | 0.5% | 0.5% | 3.1% | 7.3% | 21.4% | 40.1% | |
| Speedy True Blue | VI171 | 1.6% | 3.6% | 15.6% | 26.6% | 54.7% | 70.8% | NCIMB deposit nr 41932 |
| Speedy Yellow and Purple | VL983 | 7.8% | 14.6% | 29.2% | 41.7% | 62.0% | 70.8% | |
| Delta Premium Yellow Blotch | VM788 | 0.0% | 0.0% | 0.0% | 0.0% | 2.6% | 4.7% | |
| Delta Gold with Blotch | VL163 | 0.0% | 2.1% | 4.7% | 7.8% | 30.2% | 37.0% | |
| MG II White with Blotch | | 0.0% | 0.5% | 1.6% | 3.1% | 4.2% | 30.2% | |
| Crystal bowl supr. new clr. face mix (N = 1) | | 0.0% | 0.0% | 2.1% | 4.2% | 7.3% | 14.6% | No yellow flowering plants were mature |

The following fertilization rates were applied between week 43 of 2012 and week 8 of 2013. Watering target was medium wet to wet.

TABLE 4

| Fertilization applied | N-P-K Ratio* | EC |
|---|---|---|
| Week 43 | 13-5-20 | 1.5 |
| Week 44 | 13-5-20 | 1.5 |
| Week 45 | 13-5-20 | 1.5 |
| Week 46 | 13-5-20 | 1.5 |
| Week 47 | 13-5-20 | 1.5 |
| Week 48 | 13-5-20 | 1.5 |
| Week 49 | 13-5-20 | 1.5 |
| Week 50 | 13-5-20 | 1.9 |
| Week 51 | 13-5-20 | 1.9 |
| Week 52 | 13-5-20 | 1.9 |
| Week 1 | 13-5-20 | 1.9 |
| Week 2 | 13-5-20 | 1.9 |
| Week 3 | 9-9-36 | 1.9 |
| Week 4 | 9-9-36 | 1.9 |
| Week 5 | 9-9-36 | 1.9 |
| Week 6 | 9-9-36 | 1.9 |
| Week 7 | 9-9-36 | 1.9 |
| Week 8 | 9-9-36 | 1.9 |

*N = nitrogen; P = phosphorus; K = potassium

The soil in which the plants were grown had the characteristics shown in the table below

TABLE 5

| Average Soil Analysis N = 2 | | Jan. 28, 2013 | Feb. 18, 2013 |
|---|---|---|---|
| pH | | 5.9 | 6.2 |
| EC | mS/cm 25° C. | 1.1 | 1.1 |
| $NH_4$ | mmol/l. | <0.1 | 0.1 |
| K | mmol/l. | 1.9 | 2.7 |
| Na | mmol/l. | 0.8 | 0.9 |
| Ca | mmol/l. | 1.9 | 1.8 |
| M | mmol/l. | 1.5 | 1.5 |
| $NO_3$ | mmol/l. | 7.0 | 6.1 |
| Cl | mmol/l. | 0.4 | 0.4 |
| S | mmol/l. | 0.8 | 1.1 |
| $HCO_3$ | mmol/l. | <0.1 | <0.1 |
| P | mmol/l. | 0.38 | 0.55 |
| Fe | µmol/l. | 16 | 18 |
| Mn | µmol/l. | 4.7 | 9.0 |
| Zn | µmol/l. | 6.0 | 9.4 |
| B | µmol/l. | 10.5 | 11.5 |
| Cu | µmol/l. | 1.0 | 1.9 |
| Mo | µmol/l. | <0.1 | <0.1 |
| Si | mmol/l. | 0.1 | 0.1 |

The climate in which the plants were grown is shown below

TABLE 6

| Average Climate Data N = 2 | PAR (µmol/m²s) | Humidity (%) | Temperature (° C.) |
|---|---|---|---|
| Week 43 | | | 18.0 |
| Week 44 | 72.2 | 54.8 | 17.9 |
| Week 45 | 80.7 | 60.8 | 18.0 |
| Week 46 | 79.7 | 57.2 | 17.7 |
| Week 47 | 76.4 | 56.9 | 17.8 |
| Week 48 | 29.8 | 63.9 | 13.6 |
| Week 49 | 20.9 | 59.8 | 10.9 |
| Week 50 | 21.5 | 65.8 | 11.6 |
| Week 51 | 14.1 | 74.5 | 11.5 |
| Week 52 | 18.0 | 75.2 | 11.7 |
| Week 1 | 19.0 | 80.5 | 11.3 |
| Week 2 | 19.3 | 73.2 | 10.5 |
| Week 3 | 29.8 | 66.2 | 9.7 |
| Week 4 | 29.4 | 69.2 | 9.4 |
| Week 5 | 37.5 | 75.2 | 10.7 |
| Week 6 | 55.6 | 70.4 | 10.6 |
| Week 7 | 63.0 | 70.4 | 10.3 |
| Week 8 | 71.8 | 67.4 | 10.8 |
| Weighted average | 35.9 | 69.2 | 12.0 |

The invention claimed is:

1. A pansy seed belonging to the species *Viola×wittrockiana* designated Speedy Rose Medley, representative seed of which has been deposited at NCIMB under deposit number NCIMB 41931.

2. A pansy plant belonging to the species *Viola×wittrockiana* or a plant part thereof, produced by growing the seed of claim 1.

3. The plant part of claim 2, wherein said plant part is selected from the group consisting of propagated cuttings, seed and pollen.

4. A plant according to claim 2, wherein said plant is capable of reaching maturity between 89 days and 121 days after sowing.

5. A method for producing hybrid pansy seed comprising crossing a first parent pansy plant with a second parent pansy plant and harvesting the resultant hybrid pansy seed, wherein said first parent pansy plant and/or second parent pansy plant is the pansy plant of claim 2.

* * * * *